US010947497B2

(12) United States Patent
Kim et al.

(10) Patent No.: US 10,947,497 B2
(45) Date of Patent: Mar. 16, 2021

(54) NELUMBO NUCIFERA CALLUS EXTRACT HAVING INCREASED CONTENT OF GALLIC ACID, METHOD FOR PREPARING SAME, AND WHITENING COSMETIC COMPOSITION CONTAINING SAME

(71) Applicants: Celltrion Inc., Incheon (KR); BIO-FD&C Co., Ltd., Incheon (KR)

(72) Inventors: Yeon Sook Kim, Gyeonggi-do (KR); Jung Yeon Kim, Incheon (KR); Jae Hun Kim, Gyeonggi-do (KR); Hyeong Mi Kim, Gyeonggi-do (KR); Jung Soo Bae, Seoul (KR); Jung Yun Kim, Incheon (KR); Ju Yeon Kim, Incheon (KR); Joo Hyuck Lim, Incheon (KR); Seung Ki Lee, Incheon (KR); Sung Ho Moon, Gyeonggi-do (KR); Shin Jae Chang, Incheon (KR); Sang Hyun Moh, Gyeonggi-do (KR); Jeong Hun Lee, Gyeonggi-do (KR); Hyo Hyun Seo, Incheon (KR); Ji Hong Moh, Incheon (KR); Soo Yun Kim, Incheon (KR); Jeong Gon Park, Gyeonggi-do (KR)

(73) Assignees: Celltrion Inc., Incheon (KR); BIO-FD&C Co., Ltd., Incheon (KR)

( * ) Notice: Subject to any disclaimer, the term of this patent is extended or adjusted under 35 U.S.C. 154(b) by 0 days.

(21) Appl. No.: 16/089,895

(22) PCT Filed: Mar. 30, 2017

(86) PCT No.: PCT/KR2017/003472
§ 371 (c)(1),
(2) Date: Sep. 28, 2018

(87) PCT Pub. No.: WO2017/171423
PCT Pub. Date: Oct. 5, 2017

(65) Prior Publication Data
US 2019/0194603 A1 Jun. 27, 2019

(30) Foreign Application Priority Data

Mar. 30, 2016 (KR) .................... 10-2016-0038168

(51) Int. Cl.
| | | |
|---|---|---|
| *C12N 5/00* | (2006.01) | |
| *A61K 8/368* | (2006.01) | |
| *A61Q 19/02* | (2006.01) | |
| *A61K 8/97* | (2017.01) | |
| *A61K 8/9789* | (2017.01) | |
| *C12N 5/04* | (2006.01) | |

(52) U.S. Cl.
CPC ............ *C12N 5/0025* (2013.01); *A61K 8/368* (2013.01); *A61K 8/97* (2013.01); *A61K 8/9789* (2017.08); *A61Q 19/02* (2013.01); *C12N 5/04* (2013.01); *C12N 2501/999* (2013.01)

(58) Field of Classification Search
CPC .......................... C12N 5/0025; A61K 8/9789
See application file for complete search history.

(56) References Cited

U.S. PATENT DOCUMENTS

| 2005/0265953 A1 | 12/2005 | Ennamany et al. |
| 2009/0148544 A1 | 6/2009 | Archambault et al. |

FOREIGN PATENT DOCUMENTS

| CN | 102191214 | 9/2011 |
| CN | 104813939 | 8/2015 |
| JP | H 02180807 | 7/1990 |
| JP | H 08131183 | 5/1996 |
| JP | H 104955 | 1/1998 |
| JP | 2004175688 | 6/2004 |
| JP | 2009143912 | 7/2009 |
| KR | 10-0828193 B1 | 5/2008 |
| KR | 20110095468 | 8/2011 |
| KR | 101121883 B1 | 3/2012 |
| KR | 20120057370 | 6/2012 |
| KR | 20150027851 A | 3/2015 |
| KR | 20150065560 | 6/2015 |
| WO | WO 2005012507 A1 | 2/2005 |
| WO | WO/2017/171423 | 10/2017 |

OTHER PUBLICATIONS

Ross, I A. "Medicinal Plants of the World: vol. 2. Chemical consistutents, Traditional and Modern Medicinal Uses". New York. p. 359. (Year: 2001).*
Arunyanart and Chaitrayagun, "Induction of somatic embryogenesis in lotus (*Nelumbo nucifera* Geartn.)," Scientia Horticulturae, 105(3):411-20, Jul. 2005.
Extended European Search Report in European Application No. 17775847.1 dated Nov. 22, 2019, 7 pages.
Gundlach et al., "Jasmonic acid is a signal transducer in elicitor-induced plant cell cultures," Proceedings of the National Academy of Sciences, 89(6):2389-9, Mar. 1992.
Mukherjee et al., "The sacred lotus (*Nelumbo nucifera*)—phytochemical and therapeutic profile," Journal of Pharmacy and Pharmacology, 61(4):407-22, Apr. 2009.
Wasternack, "Jasmonates: an update on biosynthesis, signal transduction and action in plant stress response, growth and development," Annals of botany, 100(4):681-97, Oct. 2007.
XP2795168A, "Composition for use in cosmetic composition for whitening or aging prevention, comprises Ginkgoaceae cambium derived stem cells or extract, and crushed material or its culture," Database WPI, Thomson Scientific, dated Jun. 2012.
XP55634370A, "Mask," Mintel, record ID 3424391, retrieved from: URL: <http://www.gnpd.com>, Sep. 2015, 5 pages.

(Continued)

*Primary Examiner* — Amy L Clark
(74) *Attorney, Agent, or Firm* — Fish & Richardson P.C.

(57) ABSTRACT

The present invention relates to *Nelumbo nucifera* callus having an increased content of gallic acid or an extract thereof and to a method for preparing the same. The *Nelumbo nucifera* callus extract according to the present invention has an excellent whitening effect by containing a large amount of gallic acid, and thus can be advantageously used as a cosmetic composition.

5 Claims, 3 Drawing Sheets

(56) References Cited

OTHER PUBLICATIONS

Yamane, "Jasmonic acid and phytoalexin," Journal of the Japanese Society of Agricultural Chemistry, 72 (5): 665-8, May 1998, (Machine Translation).

International Search Report for App No. PCT/KR2017/003472 dated Sep. 12, 2017 (2 pages).

Liu, et al., *Induction and quantitative proteomic analysis of cell dedifferentiation during callus formation of lotus (Nelumbo nucifera Gaertn.spp. baijianlian)*, J Proteomics, Oct. 13, 2015 (online), vol. 131, p. 61-70.

Lotan et al., *Stimulation of Melanogenesis in a Human Melanoma Cell Line by Retinoids*, Cancer Res., 40:3345-3350, 1980.

CN Office Action for App No. CN 2017800215880, dated Dec. 1, 2020 (with English translation) (10 pages).

Haiyan Li et al., Establishment of Callus Regeneration System for Acer ginnala Maxim and Determination of Gallic Acid in Callus, Chinese Bulletin of Botany, 25(2):212-219 (2008) (with English Abstract).

Huang, Su-ying, et al., "Extraction of lotus seed polyphenols by microwave technique with ethanol [J]." Subtropical Agriculture Research 3 (2009) (4 pages) (with English Abstract).

* cited by examiner

*NELUMBO NUCIFERA* CALLUS EXTRACT HAVING INCREASED CONTENT OF GALLIC ACID, METHOD FOR PREPARING SAME, AND WHITENING COSMETIC COMPOSITION CONTAINING SAME

TECHNICAL FIELD

The present invention relates to a *Nelumbo nucifera* callus extract having an increased gallic acid content and to a preparation method thereof. Moreover, the present invention relates to a cosmetic composition having an excellent skin whitening effect, which comprises the extract.

BACKGROUND ART

Melanism of the skin is caused by the response of skin cells to intrinsic and extrinsic factors and is typically caused by exposure of the skin to UV rays. Namely, when the skin is exposed to UV rays, tyrosinase is activated, which acts on tyrosine, a kind of amino acid present in skin tissue, thereby producing DOPA. The DOPA is oxidized to dopaquinone which then polymerizes into melanin in melanosomes in melanocytes which are skin pigment cells. This melanin migrates to keratinocytes (skin keratin-forming cells), reaches the skin surface by keratinization and protects the skin from UV rays.

Melanin is an essential UV absorber for the human body and functions as a free-radical scavenger effective in removing various radicals that modify bio-materials such as proteins, lipids, nucleic acids and the like. However, when melanin is excessively synthesized locally, or when the skin's physiological functions are reduced due to skin lesions and aging, melanin is deposited on the skin surface, causing spots, freckles and various pigmentations.

As the causes and mechanisms of this melanism of the skin have been revealed, a method of adding, to cosmetic compositions, materials having the effect of inhibiting tyrosinase which is involved in the melanism process, or a method of reducing melanin production by inhibiting some reactions during melanin production, has generally been used to prevent melanism of the skin.

Representative substances, which are used for this purpose, include arbutin, ascorbic acid, hydroquinone and the like. Arbutin has an excellent effect of inhibiting tyrosinase activity, but has problems in terms of stability because when it is added to cosmetic products, it is discolored and the potency thereof is reduced with the passage of time. In addition, arbutin has limited uses due to its high skin irritability. Ascorbic acid has problems in that it has a low effect on the inhibition of tyrosinase activity and is not suitable as a melanin production inhibitor because the stability of the molecule itself is low. Hydroquinone has a problem in that it is highly irritating to the skin, and thus the use thereof in cosmetic formulations is currently limited due to safety issues.

Meanwhile, as it has been revealed that plant extracts of natural origin contain active ingredients that exhibit various physiological activities, there has been interest in plant extracts which can substitute for whitening substances and exhibit proper whitening effects.

In efforts to find plant extracts that exhibit whitening effects, there is a study on the use of a *Nelumbo nucifera* extract (Korean Patent No. 0828193). However, in this case, there are problems in that a process of directly cultivating *Nelumbo nucifera* is required indicating that there are temporal and spatial limitations, and in that an active ingredient having sufficient activity is not obtained by simple extraction.

To overcome the limitations, interest in the use of *Nelumbo nucifera* callus is increasing. However, conventional *Nelumbo nucifera* callus extracts have problems in that they are not effective at low concentrations and show insignificant whitening effects in actual clinical tests on the human skin.

DISCLOSURE

Technical Problem

Accordingly, the present inventors have conducted studies to obtain a *Nelumbo nucifera* callus extract having a maximized whitening effect, and as a result, a *Nelumbo nucifera* callus derived from *Nelumbo nucifera* tissue was cultivated in a medium containing methyl jasmonic acid, and the *Nelumbo nucifera* callus extract was produced with increased gallic acid content, and have found that the *Nelumbo nucifera* callus extract having an increased gallic acid content has an excellent whitening effect, thereby completing the present invention.

Therefore, it is one objective of the present invention to provide a *Nelumbo nucifera* callus or an extract thereof, which has an increased gallic acid content.

Another objective of the present invention is to provide a method of increasing the content of gallic acid in a *Nelumbo nucifera* callus or an extract thereof.

Yet another objective of the present invention is to provide a method for preparing a *Nelumbo nucifera* callus extract having an increased gallic acid content.

Still yet another objective of the present invention is to provide a whitening cosmetic composition containing, as an active ingredient, the *Nelumbo nucifera* callus extract having an increased gallic acid content.

Technical Solution

To achieve objectives, the present invention provides a *Nelumbo nucifera* callus or an extract thereof, which has an increased gallic acid content, a preparation method thereof, and a cosmetic composition having an excellent skin whitening effect, which comprises the extract.

Hereinafter, the present invention will be described in more detail.

The present invention provides a *Nelumbo nucifera* callus or an extract thereof, which has an increased gallic acid content.

*Nelumbo nucifera* is a perennial plant that grows in ponds. Its roots spread sideways, are columnar in shape, have many nodes, and their ends become thicker, particularly in autumn. The leaves sprout from the rhizome, rise above the water surface, have a shape close to a circle, have veins spreading all over, are about 40 cm in diameter, are not easily wet with water, and have thorn like projections at the veins. The flowers bloom in red or white in July to August, and are 15 to 20 cm in diameter. The flower stalks have thorns like petioles, and have one flower at the end. The fruits ripen in October, are elliptical in shape, about 2 cm in length, and eatable. The fruits or seeds of *Nelumbo nucifera* are called lotus seeds; the green embryos in the mature seeds of *Nelumbo nucifera* are called lotus seed embryos; the white grains in the mature seeds of *Nelumbo nucifera* are called lotus seed flesh; the stamens of *Nelumbo nucifera* are called lotus stamens; the leaves are called lotus leaves; the rhizome is called lotus root; and the node of the rhizome are called lotus root node. It is well known that the lotus leaves are used for diarrhea, headache, dizziness, hematemesis, postpartum hemorrhage treatment, enuresis, and detoxification.

The *Nelumbo nucifera* callus that is used in the present invention is derived from the seed of lotus called "Ara Hongnyon" in Korean, but is not limited thereto. "Ara Hongnyon" refers to a lotus plant grown from an about 700-year-old seed which was excavated from the Seongsan mountain fortress, Haman, Gyeongsangnam-do, Korea. It is also called Haman Lotus. The Ara Hongnyon lotus is a light cherry red flower having petals, which can be seen in Buddhist paintings of the Goryeo Dynasty. It is characterized by the color gradually becoming thinner every time the petal shrinks and spreads, leaving a dark red color only at the end of the petal. The pure white color of the petal roots is gradually becoming more cherry-reddish along the petals, and the simple and elegant shape of the long petal is proud of its unrivaled figure which is not comparable with that of current lotus flowers.

The callus refers to a specific tissue or cell mass produced when a tissue cut from a plant is cultured in a medium containing auxin, or any kind of plant is wounded, or a wound site is treated with auxin. Usually callus is an amorphous tissue or cell mass that has lost its ability to cause normal organogenesis or tissue differentiation, and consists mostly of parenchyma cells. In a broad sense, it also includes plant tumor tissue caused by infection with *Agrobacterium* or the like.

In other words, the cells in a plant are directed immediately after proliferation, and are assembled regularly into specific tissues and organs. However, it is believed that when callus, an undifferentiated cell mass formed through tissue culture, is externally stimulated by a variety of plant growth hormones, the control that has been maintained until then is released and the cells proliferate randomly.

When the callus obtained by dedifferentiation is added to and shake-cultured in a liquid medium having the same composition, the cells are kept apart from each other and continue to proliferate in a suspended state. The callus or cultured cell can permanently divide and proliferate by subculturing in a fresh medium, and thus are essentially different from differentiated cells by which the whole plant ages and dies. When the callus or cells subcultured for several passages are applied on a solid medium from which various plant growth hormones were removed, buds and roots sprout and an individual plant is restored. The regenerated plant originates from the division and proliferation of one cultured cells, and the cultured cell originates from the hypocotyl or other tissue.

In the present invention, "*Nelumbo nucifera* callus" may be derived from any part of *Nelumbo nucifera*. In one embodiment, it may be a callus derived from a seed leaf (cotyledon) cut from a seedling germinated from a *Nelumbo nucifera* seed. When a part cut from any tissue of *Nelumbo nucifera* is placed in a medium having controlled contents of auxin and cytokine, a callus may be formed.

In the present invention, "*Nelumbo nucifera* callus culture" is one obtained by culturing *Nelumbo nucifera* callus in a medium. As the medium, any medium that is generally used in callus culture in the technical field may be used without limitations.

The gallic acid has a structure represented by the following Formula 1:

Formula 1

The gallic acid is a kind of secondary metabolite which is produced as a by-product during normal metabolism of plant cells and accumulates in a special place in the cell. The gallic acid is known to have a whitening effect.

In the present invention, the *Nelumbo nucifera* callus having an increased gallic acid content may be prepared by culturing *Nelumbo nucifera* callus in a medium containing methyl jasmonic acid. The *Nelumbo nucifera* callus extract having an increased gallic acid content may be prepared by culturing *Nelumbo nucifera* callus in a medium containing methyl jasmonic acid, followed by extraction.

The methyl jasmonic acid is an elicitor which is used to increase the content of the secondary metabolite gallic acid. *Nelumbo nucifera* callus may be cultured in a medium containing 100 to 400 μM of methyl jasmonic acid, specifically a medium containing 100 to 250 μM of methyl jasmonic acid, more specifically a medium containing 200 μM of methyl jasmonic acid, but is not limited thereto. If the concentration of methyl jasmonic acid in the medium is less than 100 μM, it will have no significant effect on changes in the contents of physiologically active substances, whereas if the concentration of methyl jasmonic acid in the medium is more than 400 μM, it will difficult to maintain the *Nelumbo nucifera* callus, due to browning of the callus.

In the present invention, the "elicitor" is a plant immunity-activating substance that increases various defense mechanisms of the plant.

The *Nelumbo nucifera* callus or its extract, which has an increased gallic acid content, may contain gallic acid in an amount of 0.01 to 10 wt %, more specifically 0.1 to 3 wt %, based on the total weight of the extract, but is not limited thereto.

The *Nelumbo nucifera* callus having an increased gallic acid content, a lysate thereof, an extract thereof, or a culture thereof may be contained in a composition.

In the present invention, the "lysate" refers to a cell lysate obtained by lysing the callus using a chemical or physical method, and the "extract" is a substance obtained by dissolving the callus in a solvent, followed by separation, and may be concentrated by distillation or evaporation. In addition, the "culture" is a substance containing a culture broth and/or a cultured callus.

In one embodiment of the present invention, it was shown that a *Nelumbo nucifera* callus extract obtained by culturing a *Nelumbo nucifera* callus in a medium containing methyl jasmonic acid, followed by extraction, had an increased gallic acid content. In particular, it was shown that a *Nelumbo nucifera* callus extract obtained by culturing in a medium containing 200 μM of methyl jasmonic acid had the highest gallic acid content.

In one embodiment of the present invention, it was shown that the gallic acid content of a *Nelumbo nucifera* callus extract obtained by culturing in a medium containing methyl jasmonic acid was at least 10-fold higher than that of a *Nelumbo nucifera* callus cultured in a medium containing no methyl jasmonic acid.

The present invention also provides a method for preparing a *Nelumbo nucifera* callus extract having an increased gallic acid content, the method comprising the steps of:

(a) germinating a *Nelumbo nucifera* seed;

(b) inducing a *Nelumbo nucifera* callus from the germinated *Nelumbo nucifera* tissue;

(c) culturing the *Nelumbo nucifera* callus in a medium containing methyl jasmonic acid; and (d) extracting the *Nelumbo nucifera* callus culture having an increased gallic acid content.

In the preparation method according to the present invention, in order to germinate the *Nelumbo nucifera* seed and derived the callus in step (b), a suitable medium may be selected. Any medium which is generally used in callus culture in the technical field may be used without limitations. For plants, MS (Murashige-Skoog) medium, B5 medium and the like are generally used. The composition of MS basal solid medium (Murashige and Skoog 1962, Duchefa, Cat No. M0221) comprises, per liter, 1650 mg $NH_4NO_3$, 1900 mg $KNO_3$, 440 mg $CaCl_2.2H_2O$, 370 mg $MgSO_4.7H_2O$, 170 mg $KH_2PO_4$, 0.83 mg KI, 6.2 mg $H_3BO_3$, 22.3 mg $MnSO_4.4H_2O$, 8.6 mg $ZnSO_4.7H_2O$, 0.25 mg $Na_2MoO_4.2H_2O$, 0.025 mg $CuSO_4.5H_2O$, 0.025 mg $CoCl_2.6H_2O$, 27.8 mg $FeSO_4.7H_2O$, 37.3 mg $Na_2EDTA.2H_2O$, 100 mg myoinositol, 0.5 mg nicotinic acid, 0.5 mg pyridoxine-HCl, 0.5 mg thiamine-HCl, 2 mg glycine, and 30000 mg sucrose.

In one embodiment of the present invention, as a medium for inducing the callus from the *Nelumbo nucifera* seed, a medium obtained by adding 40.0 g/L sucrose, 5-10.0 g/L agar, 0.5 mg/L α-naphthaleneacetic acid (NAA) and 1.0 mg/L 6-benzylaminopurine to the MS basal solid medium may be used. In this regard, the pH of the medium is 5.5 to 6.0. More specifically, the pH is 5.7 to 5.8.

In the preparation method according to the present invention, in order to increase the content of the secondary metabolite gallic acid in step (c), the *Nelumbo nucifera* callus may be cultured in a medium containing 100 to 400 μM of methyl jasmonic acid, specifically a medium containing 100 to 250 μM of methyl jasmonic acid, more specifically a medium containing 200 μM of methyl jasmonic acid, but is not limited thereto.

As the medium containing methyl jasmonic acid, any medium which is generally used in callus culture in the technical field may be used without limitations.

In one embodiment of the present invention, it was shown that the gallic acid content of a *Nelumbo nucifera* callus extract obtained by culturing in a medium containing methyl jasmonic acid as an elicitor was increased compared to that of general *Nelumbo nucifera* callus extracts. In particular, it was shown that a *Nelumbo nucifera* callus extract obtained by culturing in a medium containing 200 μM of methyl jasmonic acid had the highest gallic acid content.

Methyl jasmonic acid is preferably added to the medium at 4 to 6 weeks from the start of the culturing in step (c). If methyl jasmonic acid is added before 4 weeks, the *Nelumbo nucifera* cells cannot be sufficiently cultured, and thus the callus cannot be sufficiently produced. If methyl jasmonic acid is added after 6 weeks, the amount of the *Nelumbo nucifera* cells can be so large that it cannot be suitable for inducing the callus from the *Nelumbo nucifera* cells. More preferably, methyl jasmonic acid may be added at 5 weeks from the start of the culturing.

In the preparation method according to the present invention, the extraction in step (d) may be performed by filtration, hot-water extraction, ethanol extraction, dipping extraction, reflux cooling extraction, ultrasonic extraction, or supercritical extraction, more specifically hot-water extraction, but is not limited thereto.

In the preparation method according to the present invention, the extract obtained in step (d) may contain gallic acid in an amount of 0.01 to 10 wt %, more specifically 0.1 to 3 wt %, based on the total weight of the extract, but is not limited thereto.

The present invention also provides a whitening cosmetic composition containing, as an active ingredient, a *Nelumbo nucifera* callus extract having an increased gallic acid content.

The composition may contain the *Nelumbo nucifera* callus extract having an increased gallic acid content in an amount of 0.1 to 30 wt % based on the total weight of the composition. If the content of the extract is less than 0.1 wt %, it will not exhibit an improved skin whitening effect, and if the content of the extract is more than 30 wt %, the improvement in skin whitening effect by an increase in the content will be insignificant, there will be a problem in formulation safety and stability, and it will not be economical.

When the cosmetic composition of the present invention is formulated as a paste, cream or gel, a carrier component that may be used is animal oil, vegetable oil, wax, paraffin, starch, tragacanth, cellulose derivatives, polyethylene glycol, silicone, bentonite, silica, talc, zinc oxide or the like.

When the cosmetic composition of the present invention is formulated as a solution or an emulsion, a carrier component that may be used is a solvent, a solubilizer or a emulsifier. For example, the carrier component used may be water, ethanol, isopropanol, ethyl carbonate, ethyl acetate, benzyl alcohol, benzyl benzoate, propylene glycol, 1,3-butylene glycol oil, glycerol aliphatic ester, polyethylene glycol or sorbitan fatty acid ester.

When the cosmetic composition of the present invention is formulated as a suspension, a carrier component that may be used is a liquid diluent such as water, ethanol or propylene glycol, a emulsifier such as ethoxylated isostearyl alcohol, polyoxyethylene sorbitol ester or polyoxyethylene sorbitan ester; microcrystalline cellulose, aluminum metahydroxide, bentonite, agar, tragacanth or the like.

When the cosmetic composition of the present invention is formulated as a powder or spray, a carrier component that may be used is lactose, talc, silica, aluminum hydroxide, calcium silicate or polyamide powder. In particular, when the cosmetic composition is formulated as a spray, it may further comprise a propellant such as chlorofluorohydrocarbon, propane/butane, or dimethyl ether.

When the cosmetic composition of the present invention is formulated as a surfactant-containing cleanser, a carrier component that may be used is aliphatic alcohol sulfate, aliphatic alcohol ether sulfate, sulfosuccinic acid monoester, isethionate, an imidazolinium derivative, methyl taurate, sarcosinate, fatty acid amide ether sulfate, alkylamidobetaine, aliphatic alcohol, fatty acid glyceride, fatty acid diethanolamide, vegetable oil, a lanolin derivative, ethoxylated glycerol fatty acid ester or the like.

When the cosmetic composition of the present invention is formulated as a surfactant-containing cleansing formulation, a cleansing formulation containing no surfactant, or soap, it may be washed out, detached or washed with water after being applied to the skin. Examples of the soap include, but are not limited to, liquid soap, powder soap, solid soap and oil soap; examples of the surfactant-containing cleansing formulation include, but are not limited to, cleansing foam, cleansing water, a cleansing towel and a cleansing pack; and examples of the cleansing formulation containing no surfactant include, but are not limited to, cleansing cream, cleansing lotion, cleansing water and cleansing gel.

The cosmetic composition of the present invention may be used in combination with other cosmetic compositions. In addition, the cosmetic composition according to the present invention may be used according to a conventional method, and the frequency of use thereof may vary depending on the skin condition or preference of the user.

The cosmetic composition according to the present invention contains, as an active ingredient, a *Nelumbo nucifera* callus extract having an increased gallic acid content, which is obtained by inducing a callus from *Nelumbo nucifera* tissue and then culturing the callus in a medium containing a specific concentration of methyl jasmonic acid, followed by extraction. By virtue of this extract, the cosmetic composition exhibits an excellent skin whitening effect by inhibiting melanin production.

In the present invention, the "*Nelumbo nucifera* callus" may be derived from any part of *Nelumbo nucifera*. In one embodiment, it may be a callus derived from a seed leaf (cotyledon) cut from a seedling germinated from a *Nelumbo nucifera* seed. When a part cut from any tissue of *Nelumbo nucifera* is placed in a medium having controlled contents of auxin and cytokine, a callus may be formed.

In the present invention, the "*Nelumbo nucifera* callus culture" is one obtained by culturing a *Nelumbo nucifera* callus in a specific medium.

In the present invention, the "elicitor" is a plant immunity-activating substance that increases various defense mechanisms of the plant.

In the present invention, the expression "containing, as an active ingredient" means that the cosmetic composition contains the active ingredient such that it can exhibit a skin whitening effect by, for example, inhibiting melanin production in skin cells.

Advantageous Effects

The *Nelumbo nucifera* callus or its extract according to the present invention, which has an increased gallic acid content, contains a large amount of gallic acid, and thus exhibits a skin whitening effect by inhibiting melanin production. Accordingly, the present invention may be effectively used as a whitening cosmetic composition.

MODE FOR INVENTION

Hereinafter, the present invention will be described in detail with reference to examples.

However, the following examples are for illustrative purposes only and are not intended to limit the scope of the present invention.

Reference Example: Obtaining of *Nelumbo nucifera* Seeds

In this Example, 30 *Nelumbo nucifera* seeds, harvested during 3 years (2010 to 2012) after cultivation of an about 700-year-old lotus seed (which dates back to Korea's Goryeo Dynasty) excavated from the Haman Seongsan mountain fortress in 2009, were obtained from the Haman Museum located at Gaya-Eup, Haman-gun, Gyeongsang-nam-do, South Korea.

Example 1: Preparation of *Nelumbo nucifera* Callus

Sterilized *Nelumbo nucifera* seeds were sowed on MS (Murashige-Skoog) basal solid medium (Murashige and Skoog 1962, Duchefa, Cat No. M0221) containing no hormone and were germinated under a long-day condition (18 hours) at 25 to 28° C.

The cotyledon attached to the germinated seedling was cut about 3-5 cm with a sharp knife and placed on an MS basal solid medium (pH 5.8) obtained by adding 40.0 g/L sucrose, 5-10.0 g/L agar, 0.5 mg/L α-naphthaleneacetic acid and 1.0 mg/L 6-benzylaminopurine to MS basal solid medium (Murashige and Skoog 1962, Duchefa, Cat No. M0221). After about 2 weeks, a shoot together with a callus was produced from the hypocotyl and subcultured with a rooting medium while the callus was maintained.

On the above-described medium prepared by adding plant growth regulating substances (40.0 g/L sucrose, 5-10.0 g/L agar, 0.5 mg/L α-naphthaleneacetic acid and 1.0 mg/L 6-benzylaminopurine to MS basal solid medium) to MS basal solid medium, culture was performed at 25° C. for 4 weeks. At 5 weeks of the culture, methyl jasmonic acid was added to the medium at concentrations of 100 μM, 200 μM and 400 μM, followed by culture.

Example 2: Preparation of *Nelumbo nucifera* Callus Extracts

Each callus obtained as described above was harvested, washed several times with water, and dried in a vacuum freeze dryer (Ilshin, Cat no. LP-50) for 3 days. 1 kg of the dried *Nelumbo nucifera* callus was placed in a container, and 100 L of purified water was added thereto, followed by hot-water extraction at 90 to 120° for 48 hours. After the extraction, the solid was removed by filtration, thereby preparing *Nelumbo nucifera* callus extracts.

The *Nelumbo nucifera* callus extracts obtained by culturing in the media containing 100 μM, 200 μM and 400 μM of methyl jasmonic acid, respectively, were named Example 2-1, Example 2-2 and Example 2-3, respectively.

Comparative Examples 1 to 4: Preparation of Comparative Examples According to Elicitor Treatment

*Nelumbo nucifera* callus extracts were prepared by *Nelumbo nucifera* callus preparation and hot-water extraction in the same manner as described in Examples 1 and 2 above, except that the elicitor methyl jasmonic acid was not added or salicylic acid (SA) in place of methyl jasmonic acid was added to the medium at concentrations of 100 μM, 200 μM and 400 μM.

The *Nelumbo nucifera* callus extract obtained by culturing in the medium containing no methyl jasmonic acid was named Comparative Example 1, and the *Nelumbo nucifera* callus extract obtained by culturing in the media containing 100 μM, 200 μM and 400 μM of salicylic acid, respectively, were named Comparative Example 2, Comparative Example 3 and Comparative Example 4, respectively.

Comparative Examples 5 to 7: Preparation of Comparative Examples Using Various *Nelumbo nucifera* Parts without Callus Induction

*Nelumbo nucifera* seeds and leaves were collected from Haman, Korea. The *Nelumbo nucifera* leaves were dried at 55° C. for 8 hours and ground in a mixer, and 750 ml of water as an extraction solvent was added to 50 g of the ground material, followed by extraction for 6 hours. The resulting extract was named Comparative Example 5.

To obtain Comparative Examples 6 and 7, *Nelumbo nucifera* seeds were cut and separated into seed embryos and flesh, and water was added thereto, followed by extraction for 6 hours. Next, 1% filtration aid was added, followed by filtration and then drying at 80° C. The water extract of the *Nelumbo nucifera* seed embryo was named Comparative Example 6, and the water extract of the *Nelumbo nucifera* seed flesh was named Comparative Example 7.

Experimental Example 1: Analysis of Increase in Gallic Acid Content of *Nelumbo nucifera* Callus Extracts Prepared Using Different Kinds and Concentrations of Elicitor In order to examine whether the gallic acid content of the *Nelumbo nucifera* callus extracts increases depending on the kind and concentration of elicitor, the content of gallic content in each of the *Nelumbo nucifera* callus extracts prepared in Example 2 and Comparative Examples 1 to 4 was measured by HPLC.

Specifically, 0.1 g of each of lyophilisates of the *Nelumbo nucifera* callus extracts prepared in Examples 2-1, 2-2 and 2-3 above was dissolved in purified water, thereby obtaining 10 ml of each sample solution. In addition, 10 mg of a gallic acid ($C_7H_6O_5$: 170.12) standard was dissolved in purified water to a final volume of 100 ml, and then 0.5 ml of the solution was dissolved again in purified to a final volume of 100 ml and diluted to ½ and ¼, thereby obtaining standard solutions. 20 μl of each of the above-described sample solutions and standard solutions was analyzed by HPLC.

The HPLC analysis was performed using Agilent 1260 Infinity (Agilent, USA). The column used was CAPCELL PAK C18 UG120 (250 mm×4.6 mm; 5 μm). As a mobile phase, a mixture of 0.1% trifluoroacetic acid (TFA) and 0.1% acetonitrile (B) was used. The content of B was increased from 0% to 90% with a constant gradient over 35 minutes. The flow rate was 1.0 ml/min, and the detection wavelength of the UV detector was set at 270 nm. The gallic acid content of each of the *Nelumbo nucifera* callus extracts, measured by HPLC, is shown in FIGS. 1 and 2 and Table 1 below.

TABLE 1

| *Nelumbo nucifera* callus extract | Methyl jasmonic acid concentration (μM) | Salicylic acid concentration (μM) | Gallic acid (μg/mg) | Wt % |
|---|---|---|---|---|
| Example 2-1 | 100 | — | 7.36 | 0.74 |
| Example 2-2 | 200 | — | 27.83 | 2.78 |
| Example 2-3 | 400 | — | 14.18 | 1.42 |
| Comparative Example 1 | — | — | 0.00 | 0.00 |
| Comparative Example 2 | — | 100 | 0.00 | 0.00 |
| Comparative Example 3 | — | 200 | 0.00 | 0.00 |
| Comparative Example 4 | — | 400 | 0.00 | 0.00 |

Figure 1:
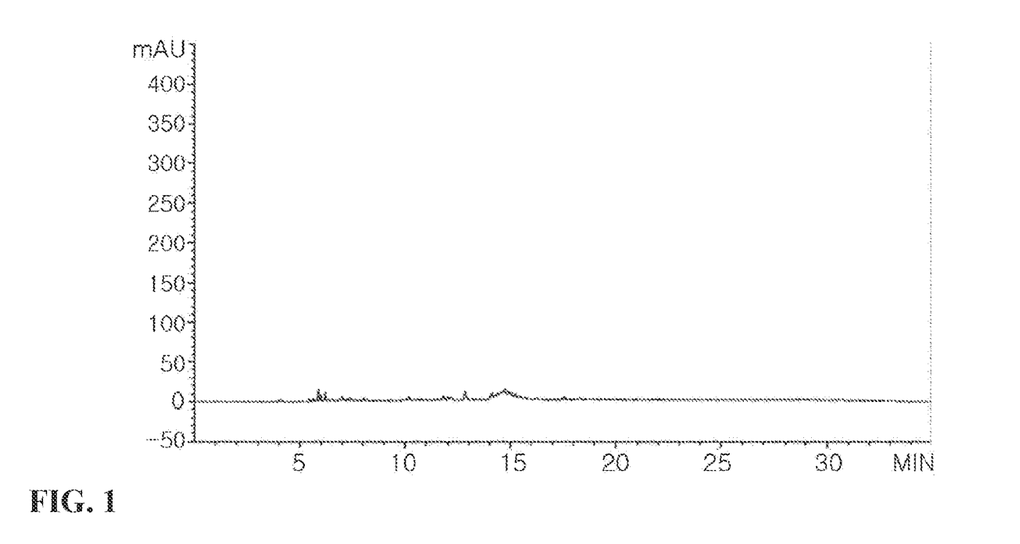
FIG. 1 shows the results of HPLC analysis performed to analyze the gallic acid content of a *Nelumbo nucifera* callus extract prepared in Comparative Example 1.
Figure 2:
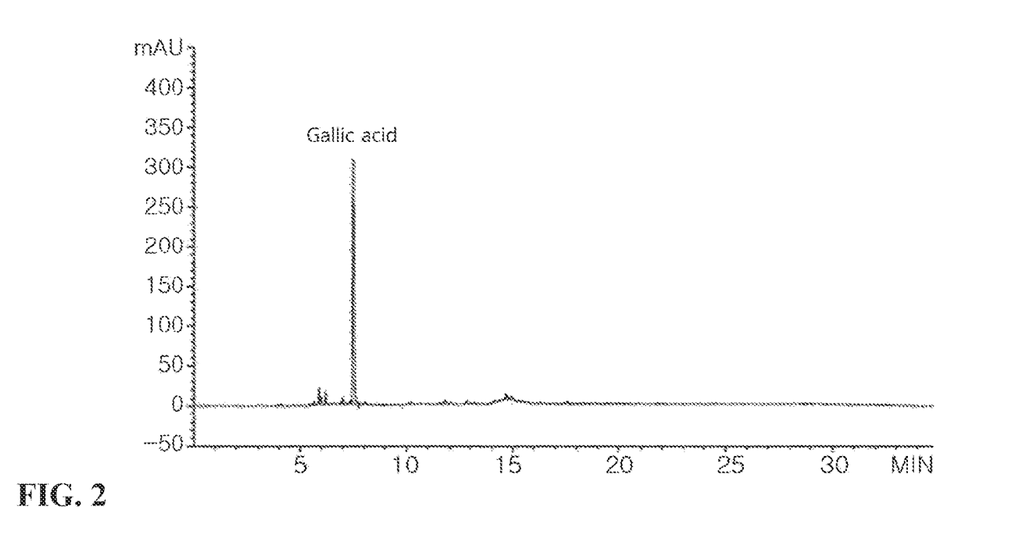
FIG. 2 shows the results of HPLC analysis performed to analyze the gallic acid content of a *Nelumbo nucifera* callus extract prepared in Example 2-2.

As a result, as shown in FIGS. 1 and 2, no gallic acid was detected in the *Nelumbo nucifera* callus extract prepared in Comparative Example 1 (FIG. 1), whereas gallic acid was detected in the *Nelumbo nucifera* callus extract prepared through treatment with methyl jasmonic acid in Example 2-2 (FIG. 2).

In addition, as shown in Table 1 above, the results of HPLC indicated that the peak of gallic acid did not appear not only in the *Nelumbo nucifera* callus extract prepared in Comparative Example 1, but also in Comparative Examples 2 to 4 in which treatment with salicylic acid was performed, indicating that no gallic acid was also detected in the *Nelumbo nucifera* callus extracts obtained through treatment with salicylic acid.

However, it was shown that the *Nelumbo nucifera* callus extracts prepared through treatment with methyl jasmonic acid in Examples 2-1 to 2-3 had increased gallic acid contents. In particular, it was shown that the *Nelumbo nucifera* callus extract prepared by culturing in the medium containing 200 μM of methyl jasmonic acid (Example 2-2) had the highest gallic acid content.

Experimental Example 2: Analysis of Gallic Acid Content in Extract Prepared from Each *Nelumbo nucifera* Part without Callus Induction In order to measure the gallic acid contents of the extract samples of Example 2-2 and Comparative Examples 5 to 7, HPLC analysis was performed.

Figure 3:
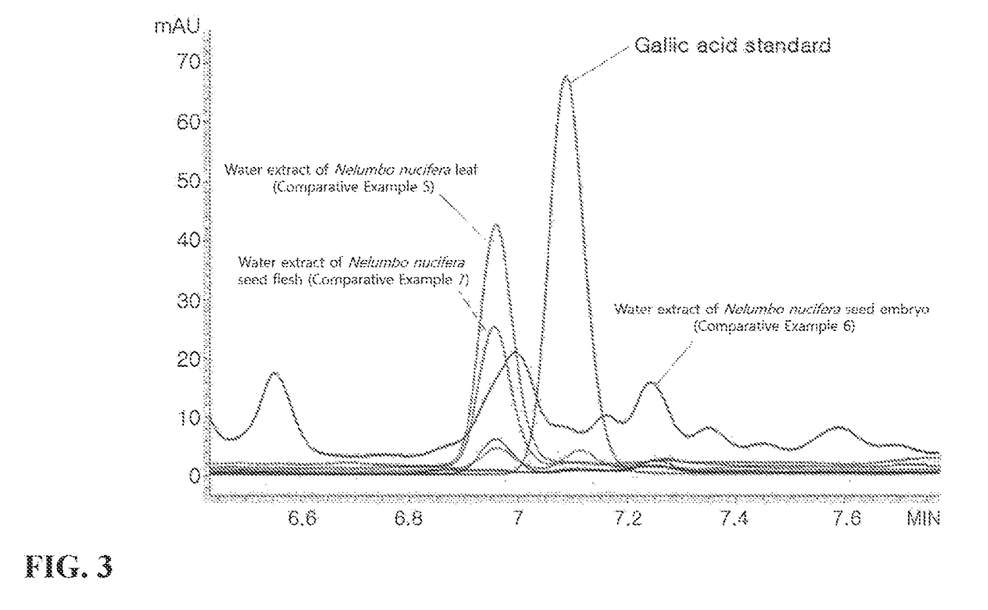
FIG. 3 shows the results of HPLC analysis performed to analyze the gallic acid contents of *Nelumbo nucifera* extracts prepared without callus induction (Comparative Examples 5 to 7).

The HPLC analysis was performed using Agilent 1260 Infinity (Agilent, USA). The column used was CAPCELL PAK C18 UG120 (250 mm×4.6 mm; 5 μm). As a mobile phase, a mixture of 0.1% trifluoroacetic acid (TFA) and 0.1% acetonitrile (B) was used. The content of B was increased from 0% to 90% with a constant gradient over 35 minutes. The flow rate was 1.0 ml/min, and the detection wavelength of the UV detector was set at 270 nm. The gallic acid content of each of the extracts of Comparative Examples 5 to 7, measured by HPLC, is shown in FIG. 3.

TABLE 2

| Test group | Gallic acid (μg/mg) |
|---|---|
| Example 2-2 (*Nelumbo nucifera* callus extract prepared through treatment with 200 μM of methyl jasmonic acid) | 27.83 |
| Comparative Example 5 (water extract of *Nelumbo nucifera* leaf) | 0.00 |
| Comparative Example 6 (water extract of *Nelumbo nucifera* seed embryo) | 0.00 |

TABLE 2-continued

| Test group | Gallic acid (µg/mg) |
|---|---|
| Comparative Example 7 (water extract of *Nelumbo nucifera* seed flesh) | 0.00 |

As a result, it was shown that gallic acid was detected in the *Nelumbo nucifera* callus extract prepared in Example 2-2 (see FIG. 2), whereas no gallic acid was detected in the extracts of Comparative Examples 5 to 7, prepared without callus induction (see FIG. 3). The gallic acid content of Example 2-2 and Comparative Examples 5 to 7 are shown in Table 2 above.

Experimental Example 3: Examination of Whitening Effect of *Nelumbo nucifera* Callus Extract Having Increased Gallic Acid Content In order to evaluate the whitening effect of the *Nelumbo nucifera* callus extract having an increased gallic acid content, prepared through treatment with methyl jasmonic acid in Example 2 above, the effect of the extract on the inhibition of melanin production was evaluated using B16F1 melanocytes.

Specifically, B16F1 melanocytes, cells of mouse origin, were obtained from the ATCC (American Type Culture Collection) and used in this Example. The B16F1 melanocytes were dispensed into a 6-well plate at a density of $2 \times 10^5$ cells per well, attached to each well, and then dispensed at a concentration that caused no toxicity. Next, the cells were treated with each of 300 µg/ml of a lyophilisate of the *Nelumbo nucifera* callus extract, prepared in Comparative Example 1, and 300 µg/ml of a lyophilisate of the *Nelumbo nucifera* callus extract having an increased gallic acid content, prepared in Example 2, and were incubated in a $CO_2$ incubator at 37° C. for 72 hours. As a control, 10 nM of α-melanocyte-stimulating hormone (α-MSH) was used and incubated in the same manner as the test substance. After 72 hours of the incubation, the cells were detached by trypsin-EDTA, counted, and then collected by centrifugation. The quantification of melanin in the cells was performed using a modification of the method of Lotan (Cancer Res., 40: 3345-3350, 1980). The cell pellets were washed once with PBS, and then 1 ml of homogenization buffer (50 mM sodium phosphate, pH 6.8, 1% Triton X-100, 2 mM PMSF) was added thereto, and the cells were lysed by vortexing for 5 minutes. To the cell filtrate obtained by centrifugation (at 3,000 rpm for 10 min), 1N NaOH (10% DMSO) was added to extract melanin. The extracted melanin was dissolved, measured for its absorbance at 490 nm by microplate reader, and then quantified, and the protein amount was measured.

Melanin production (%) in the sample was evaluated by calculating the amount of melanin per unit protein and calculating the change relative to the control by use of the following Equation 1. The results are shown in Table 3.

$$\text{Melanin production (\%)} = B/A \times 100 \quad \text{Equation 1}$$

A: the amount of melanin in control well (control)/total protein;

B: the amount of melanin in *Nelumbo nucifera* callus extract-containing well (Example)/total protein.

TABLE 3

| | Methyl jasmonic acid (µM) | Conc. (µg/ml) | aMSH level (mM) | Melanin/protein (% control) |
|---|---|---|---|---|
| Control | — | — | 10 | 100% |
| Comparative Example 1 | — | 300 | | 97% |
| Example 2-1 | 100 | | | 84% |
| Example 2-2 | 200 | | | 80% |
| Example 2-3 | 400 | | | 125% |

As a result, as shown in Table 3 above, the lyophilisate of the *Nelumbo nucifera* callus extract of Comparative Example 1 showed a melanin synthesis inhibitory effect of about 3%, which was insignificant. In comparison with this, among the lyophilisates of the *Nelumbo nucifera* callus extracts having an increased gallic acid content, the extracts prepared through treatment with 100 µM or 200 µM of methyl jasmonic acid as an elicitor in Examples 2-1 and 2-2 inhibited melanin synthesis by about 20%. However, the group treated with 400 µM of methyl jasmonic acid as an elicitor showed increased melanin synthesis, and this result was believed to be because the number of the cells was decreased due to high cytotoxicity, and thus melanin synthesis seemed to be relatively increased.

Experimental Example 4: Test for Whitening Effect on Human Skin

On 24 healthy 20-60-year old women, the whitening improvement effect of a cream containing 0.5% lyophilisate of the *Nelumbo nucifera* callus extract (prepared through treatment with 200 µM methyl jasmonic acid) was evaluated. The face of each of the selected subjects was washed with a cleanser, and then the subjects were maintained in a waiting room under constant-temperature and constant-humidity conditions (temperature: 22±2° C., and humidity: 50±10%) for 30 minutes so that the skin surface temperature and humidity would be adapted to the environment of the measurement space.

Using a cream containing 0.5% lyophilisate of the *Nelumbo nucifera* callus extract and a placebo cream, a whitening effect test was performed. On first visit, the test cream and the control cream were randomly assigned to the left and right areas of the face, and the skin brightness was measured. Thereafter, the cream formulations were applied to the left and right facial areas in the morning and evening.

After 4 and 8 weeks of use of each cream, the skin brightness (L-value) was quantitatively measured using CM-2600d (Minolta, Japan), and the skin melanin index was evaluated by measuring light, emitted at 568 nm (green), 660 nm (red) and 880 nm (infrared) from a probe and reflected from the skin, by use of a mexameter and a narrow-band reflectance spectrophotometer.

The L-value is a brightness parameter, L in the L-value indicates brightness. The L-value is expressed as a number from 0 to 100.

Instrumental evaluation was performed on visit, and the test areas were measured three times with a chromameter, and the measured values were averaged. The increase rate in the skin brightness measured using the chromameter was calculated using the following Equation 2:

$$\text{Rate of increase (\%) in } L\text{-value} = ((L\text{-value after sample application}) - (L\text{-value before sample application}))/(L\text{-value before sample application}) \times 100 \quad \text{Equation 2}$$

Figure 4:
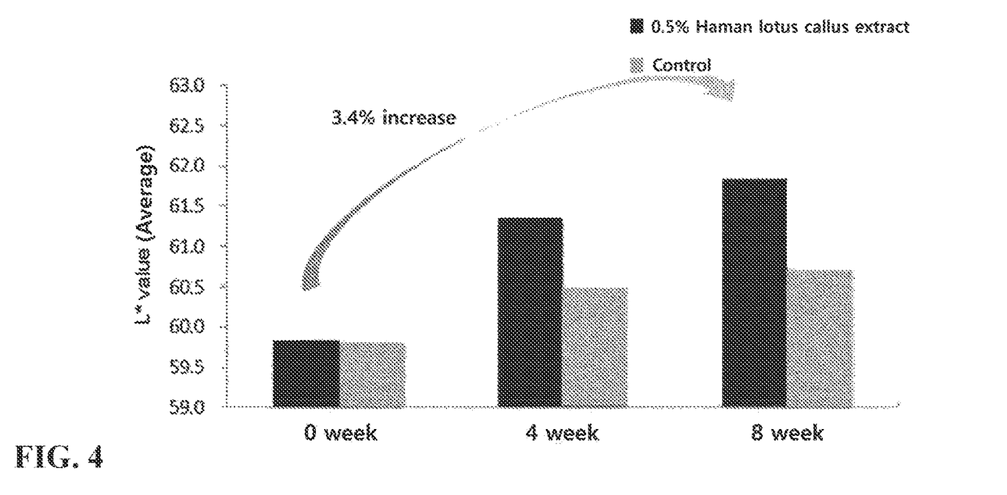
FIG. 4 shows the results of measuring a change in skin brightness (L value) after applying a cream containing 0.5% lyophilisate of a *Nelumbo nucifera* callus extract (obtained through treatment with 200 μM of methyl jasmonic acid).

As a result, as can be seen in FIG. 4, the L-value (average) measured after 8 weeks of application of the cream containing 0.5% increased from 59.8 before application to 61.8 after 8 weeks of application (3.4% increase). The P-value of the value after 8 weeks of application was less than 0.05 as tested by paired samples t-test according to normality test, indicating that the value was increased to a statistically significant level.

Figure 5:
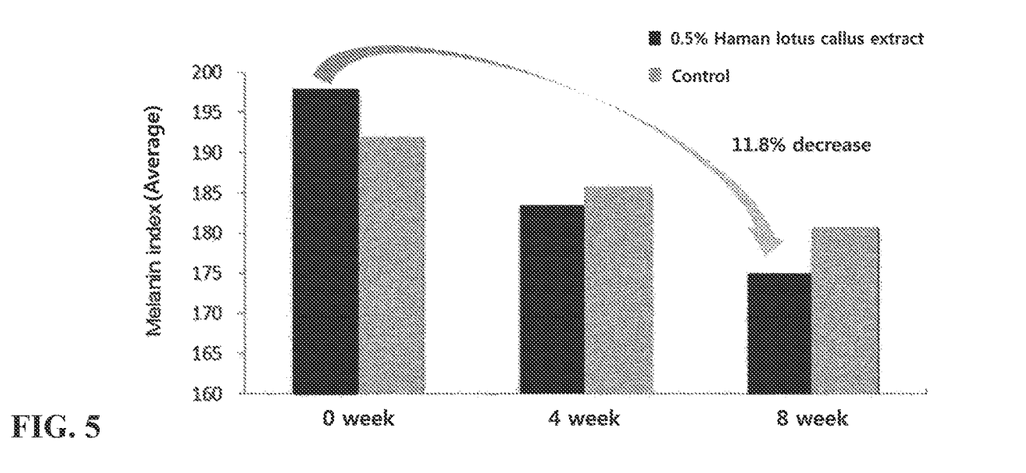
FIG. 5 shows the results of measuring a change in skin melanin index after applying a cream containing 0.5% lyophilisate of a *Nelumbo nucifera* callus extract (obtained through treatment with 200 μM of methyl jasmonic acid).

In addition, as can be seen in FIG. 5, the skin melanin index (average) decreased from 197.7 before application to 174.9 after 8 weeks of application (11.8% decrease). The P-value of the melanin index after 8 weeks of application was less than 0.05 as tested by paired samples t-test according to normality test, indicating that the value was increased to a statistically significant level.

Formulation Examples: Preparation of Formulations to Confirm Stability of Cosmetic Composition To confirm the stability of a cosmetic composition containing the *Nelumbo nucifera* callus extract having an increased gallic acid content, formulations (solubilized formulation, essence formulation and cream formulation) containing a lyophilisate of the *Nelumbo nucifera* callus extract of Example 2-2 above were prepared according to the following Formulation Examples 1 to 3.

Formulation Example 1: Preparation of Solubilized Formulation

TABLE 4

| Phase | Component | Content (%) |
|---|---|---|
| Aqueous phase | Purified water | To 100 |
| | Glycerin | 10-25 |
| | Dipropylene glycol | |
| | Betaine | |
| | D-Panthenol | |
| | Sodium hyaluronate | |
| | Thickener | q.s. |
| | Chealating agent | q.s. |
| Solubilizing phase | PEG-60 hydrogenated castor oil | 0-2 |
| | PEG-40 hydrogenated castor oil | 0-2 |
| | Polyol | 0-10 |
| | Fragrance | q.s. |
| | Ethanol | 0-20 |
| Addition I | Lyophilisate of *Nelumbo nucifera* callus extract prepared through treatment with 200 μM methyl jasmonic acid in Example 2-2 | 0.5 |
| Addition II | Preservative | q.s. |
| | Other additives | q.s. |

Preparation Method (1) The components of each of the aqueous phase and the solubilizing phase were uniformly mixed and dissolved.

(2) The solubilizing phase was added to and mixed with the aqueous phase, followed by solubilization.

(3) Addition I, a phase containing a lyophilisate of the *Nelumbo nucifera* callus extract prepared through treatment with 200 μm methyl jasmonic acid in Example 2-2, was solubilized, added and mixed, after which addition II was added.

Formulation Example 2: Preparation of Essence Formulation

TABLE 5

| Phase | Component | Content (wt %) |
|---|---|---|
| Aqueous phase | Purified water | To 100 |
| | Ceteareth-6 olivate | 0.1-3 |
| | Glycerin | 10-25 |
| | 1,2-propanediol | |
| | Sodium hyaluronate | |
| | Thickener | q.s. |
| | Chelating agent | q.s. |
| Oil phase | PEG-100 stearate | 0.1-1 |
| | Glyceryl stearate | 0.1-1 |
| | Polysorbate 60 | 0.1-1 |
| | Cetyl alcohol | 0.1-1 |
| | Behenyl alcohol | 0.1-1 |
| | Squalane | 5-20 |
| | Tocopheryl acetate | 0.1-0.5 |
| Addition phase I | Lyophilisate of *Nelumbo nucifera* callus extract prepared through treatment with 200 uM methyl jasmonic acid in Example 2-2 | 0.5 |
| Addition phase II | Fragrance | q.s. |
| | Preservative | q.s. |
| | Other additives | q.s. |

Preparation Method (1) The components of each of the aqueous phase and the oil phase were heated, mixed uniformly and mixed.

(2) At 75° C., the oil phase was added to the aqueous phase, followed by emulsification.

(3) Addition phase I, a phase containing a lyophilisate of the *Nelumbo nucifera* callus extract prepared through treatment with 200 uM methyl jasmonic acid in Example 2-2, was added and mixed at 50° C., after which addition phase II was added thereto.

Formulation Example 3: Preparation of Cream Formulation

TABLE 6

| Phase | Component | Content (wt %) |
|---|---|---|
| Aqueous phase | Purified water | To 100 |
| | Glycerin | 10-25 |
| | Betaine | |
| | Sodium hyaluronate | |
| | Thickener | q.s. |
| | Chelating agent | q.s. |
| Oil phase | PEG-100 stearate | 0.1-2 |
| | Glyceryl stearate | 0.1-2 |
| | Polysorbate 60 | 0.1-2 |
| | Stearic acid | 0.1-2 |
| | Cetearyl alcohol | 0.1-2 |
| | Capric/caprylic triglyceride | 10-30 |
| | Tocopheryl acetate | 0.1-0.5 |
| Addition I | Lyophilisate of *Nelumbo nucifera* callus extract prepared through treatment with 200 uM methyl jasmonic acid in Example 2-2 | 0.5 |

TABLE 6-continued

| Phase | Component | Content (wt %) |
|---|---|---|
| Addition II | Fragrance | q.s. |
|  | Preservative | q.s. |
|  | Other additives | q.s. |

Preparation Method (1) The components of each of the aqueous phase and the oil phase were heated, mixed uniformly and dissolved.
(2) At 75° C., the oil phase was added to the aqueous phase, followed by emulsification.
(3) Addition phase I, a phase containing a lyophilisate of the *Nelumbo nucifera* callus extract prepared through treatment with 200 uM methyl jasmonic acid in Example 2-2, was added and mixed at 50° C., after which addition phase II was added thereto.

Experimental Example 5: Evaluation of Stability of cosmetic composition containing *Nelumbo nucifera* Callus Extract Having Increased Gallic Acid Content 1) Evaluation of Raw Material Stability of *Nelumbo nucifera* Callus Extract Having Increased Gallic Acid Content To examine raw material stability, the solubilized formulation, essence formulation and cream formulation of Formulation Examples 1 to 3 were stored under conditions of 4° C., 30° C., 45° C. and sunlight for 12 weeks. Then, time-dependent changes in the gallic acid content of the lyophilisate of the *Nelumbo nucifera* callus extract having an increased gallic acid content was observed by HPLC analysis according to the same method as described in Experimental Example 1, and the results are shown in Table 7 below.

TABLE 7

| Elapsed time | Gallic acid (% relative to initial content) ||||||||||||
|---|---|---|---|---|---|---|---|---|---|---|---|---|
|  | Solubilized formulation |||| Essence formulation |||| Cream formulation ||||
|  | 4° C. | 30° C. | 45° C. | Sunlight | 4° C. | 30° C. | 45° C. | Sunlight | 4° C. | 30° C. | 45° C. | Sunlight |
| Initial | 99.9 | 100 | 99 | 99.2 | 99 | 99.8 | 100 | 99.3 | 100 | 99.5 | 99.3 | 100 |
| 1 week | 96.2 | 96.7 | 97.2 | 97 | 97.3 | 96.6 | 96 | 97.7 | 97 | 96.2 | 95.7 | 94.4 |
| 3 weeks | 97 | 97.6 | 97.3 | 94.3 | 97 | 98.1 | 98.5 | 97.1 | 96.7 | 97.7 | 98.3 | 92.4 |
| 5 weeks | 97.6 | 98.2 | 97.7 | 90.9 | 96.1 | 96.1 | 98.8 | 96.3 | 95.8 | 96.8 | 99.4 | 92 |
| 8 weeks | 96.6 | 99 | 94.6 | 86.4 | 94.3 | 96 | 96.6 | 96.9 | 96.4 | 95.2 | 100.2 | 90.9 |
| 12 weeks | 94.9 | 94.2 | 98.7 | 92.3 | 97 | 95.7 | 98.1 | 94.2 | 95.9 | 93.9 | 101.7 | 88.9 |
| Result | Stable | Stable | Stable | Stable | Stable | Stable | Stable | Stable | Stable | Stable | Stable | stable |

As a result, as shown in Table 7 above, in all the solubilized formulation, the essence formulation and the cream formulation, the active ingredient gallic acid of the lyophilisate of the *Nelumbo nucifera* callus extract having an increased gallic acid content was highly stable under high-temperature and sunlight conditions.

2) Evaluation of Formulation Stability of Cosmetic Composition Containing *Nelumbo nucifera* Callus Extract Having Increased Gallic Acid Content To evaluate formulation stability, the solubilized formulation, essence formulation and cream formulation of Formulation Examples 1 to 3 were stored under conditions of 4° C., 30° C., 45° C. and sunlight for 12 weeks. Then, changes in the color, odor and formulation were observed by visual evaluation and sensory evaluation and the results are shown in Tables 8 to 10 below. In this regard, the changes in the color, odor and formulation were evaluated according to the following criteria.

Evaluation Criteria

No change: °;
Slight change: Δ;
Significant change: X.

TABLE 8

| Elapsed time | Solubilized formulation ||||||||||||
|---|---|---|---|---|---|---|---|---|---|---|---|---|
|  | Odor change |||| Color change |||| Formulation change ||||
|  | 4° C. | 30° C. | 45° C. | Sunlight | 4° C. | 30° C. | 45° C. | Sunlight | 4° C. | 30° C. | 45° C. | Sunlight |
| 1 week | ○ | ○ | ○ | ○ | ○ | ○ | ○ | ○ | ○ | ○ | ○ | ○ |
| 2 weeks | ○ | ○ | ○ | ○ | ○ | ○ | ○ | ○ | ○ | ○ | ○ | ○ |
| 4 weeks | ○ | ○ | ○ | ○ | ○ | ○ | ○ | ○ | ○ | ○ | ○ | ○ |

TABLE 8-continued

| | Solubilized formulation | | | | | | | | | | | |
|---|---|---|---|---|---|---|---|---|---|---|---|---|
| | Odor change | | | | Color change | | | | Formulation change | | | |
| Elapsed time | 4° C. | 30° C. | 45° C. | Sunlight | 4° C. | 30° C. | 45° C. | Sunlight | 4° C. | 30° C. | 45° C. | Sunlight |
| 8 weeks | ○ | ○ | ○ | ○ | ○ | ○ | ○ | ○ | ○ | ○ | ○ | ○ |
| 12 weeks | ○ | ○ | ○ | ○ | ○ | ○ | ○ | ○ | ○ | ○ | ○ | ○ |

TABLE 9

| | Essence formulation | | | | | | | | | | | |
|---|---|---|---|---|---|---|---|---|---|---|---|---|
| | Odor change | | | | Color change | | | | Formulation change | | | |
| Elapsed time | 4° C. | 30° C. | 45° C. | Sunlight | 4° C. | 30° C. | 45° C. | Sunlight | 4° C. | 30° C. | 45° C. | Sunlight |
| 1 week | ○ | ○ | ○ | ○ | ○ | ○ | ○ | ○ | ○ | ○ | ○ | ○ |
| 2 weeks | ○ | ○ | ○ | ○ | ○ | ○ | ○ | ○ | ○ | ○ | ○ | ○ |
| 4 weeks | ○ | ○ | ○ | ○ | ○ | ○ | ○ | ○ | ○ | ○ | ○ | ○ |
| 8 weeks | ○ | ○ | ○ | ○ | ○ | ○ | ○ | ○ | ○ | ○ | ○ | ○ |
| 12 weeks | ○ | ○ | ○ | ○ | ○ | ○ | ○ | ○ | ○ | ○ | ○ | ○ |

TABLE 10

| | Cream formulation | | | | | | | | | | | |
|---|---|---|---|---|---|---|---|---|---|---|---|---|
| | Odor change | | | | Color change | | | | Formulation change | | | |
| Elapsed time | 4° C. | 30° C. | 45° C. | Sunlight | 4° C. | 30° C. | 45° C. | Sunlight | 4° C. | 30° C. | 45° C. | Sunlight |
| 1 week | ○ | ○ | ○ | ○ | ○ | ○ | ○ | ○ | ○ | ○ | ○ | ○ |
| 2 weeks | ○ | ○ | ○ | ○ | ○ | ○ | ○ | ○ | ○ | ○ | ○ | ○ |
| 4 weeks | ○ | ○ | ○ | ○ | ○ | ○ | ○ | ○ | ○ | ○ | ○ | ○ |
| 8 weeks | ○ | ○ | ○ | ○ | ○ | ○ | ○ | ○ | ○ | ○ | ○ | ○ |
| 12 weeks | ○ | ○ | ○ | ○ | ○ | ○ | ○ | ○ | ○ | ○ | ○ | ○ |

As a result, as shown in Tables 8 to 10 above, the solubilized formulation, the essence formulation and the cream formulation were all highly stable under high-temperature and sunlight conditions.

Experimental Example 6: Evaluation of Skin Irritation of Cosmetic Composition Containing *Nelumbo nucifera* Callus Extract Having Increased Gallic Acid Content In order to evaluate the skin irritation of a cosmetic composition containing the *Nelumbo nucifera* Callus extract having an increased gallic acid content, the skin irritation of the cream formulation of Formulation Example 3 was evaluated.

Specifically, a predetermined amount (20 μl) of the cream formulation (prepared in Formulation Example 3) containing the lyophilisate of the *Nelumbo nucifera* callus extract having an increased gallic acid content was applied to a 5×20 cm area on the back of each of 30 adult persons for 24 hours, and the removed. After 1 and 24 hours, changes in the skin condition were visually observed, and the results are shown in Table 11 below. In this regard, the changes in the skin condition were evaluated according to the following criteria.

Criteria for Evaluation of Skin Condition

0: no change;
1: very slight change;
2: slight change;
3: slightly serious change;
4: serious change;
5: very serious change.

TABLE 11

| Subject (sex, skin type) | Elapsed time | Skin condition at various extract contents | | |
|---|---|---|---|---|
| | | 3.2% | 6.4% | 16% |
| 1 (male, neutral) | 1 hour | 0 | 0 | 0 |
| | 24 hours | 0 | 0 | 0 |
| 2 (female, neutral) | 1 hour | 0 | 0 | 0 |
| | 24 hours | 0 | 0 | 0 |
| 3 (female, neutral) | 1 hour | 0 | 0 | 0 |
| | 24 hours | 0 | 0 | 0 |
| 4 (female, neutral) | 1 hour | 0 | 0 | 0 |
| | 24 hours | 0 | 0 | 0 |
| 5 (female, neutral) | 1 hour | 0 | 0 | 0 |
| | 24 hours | 0 | 0 | 0 |
| 6 (female, neutral) | 1 hour | 0 | 0 | 0 |
| | 24 hours | 0 | 0 | 0 |
| 7 (male, neutral) | 1 hour | 0 | 0 | 0 |
| | 24 hours | 0 | 0 | 0 |
| 8 (female, | 1 hour | 0 | 0 | 0 |

TABLE 11-continued

| Subject (sex, skin type) | Elapsed time | Skin condition at various extract contents | | |
|---|---|---|---|---|
| | | 3.2% | 6.4% | 16% |
| neutral) | 24 hours | 0 | 0 | 0 |
| 9 (female, | 1 hour | 0 | 0 | 0 |
| neutral) | 24 hours | 0 | 0 | 0 |
| 10 (female, | 1 hour | 0 | 0 | 0 |
| neutral) | 24 hours | 0 | 0 | 0 |
| 11 (female, | 1 hour | 0 | 0 | 0 |
| neutral) | 24 hours | 0 | 0 | 0 |
| 12 (female, | 1 hour | 0 | 0 | 0 |
| neutral) | 24 hours | 0 | 0 | 0 |
| 13 (female, | 1 hour | 0 | 0 | 0 |
| neutral) | 24 hours | 0 | 0 | 0 |
| 14 (female, | 1 hour | 0 | 0 | 0 |
| neutral) | 24 hours | 0 | 0 | 0 |
| 15 (female, | 1 hour | 0 | 0 | 0 |
| neutral) | 24 hours | 0 | 0 | 1 |
| 16 (female, | 1 hour | 0 | 0 | 0 |
| neutral) | 24 hours | 0 | 0 | 0 |
| 17 (female, | 1 hour | 0 | 0 | 0 |
| neutral) | 24 hours | 0 | 0 | 0 |
| 18 (female, | 1 hour | 0 | 0 | 0 |
| neutral) | 24 hours | 0 | 0 | 0 |
| 19 (female, | 1 hour | 0 | 0 | 0 |
| neutral) | 24 hours | 0 | 0 | 0 |
| 20 (female, | 1 hour | 0 | 0 | 0 |
| neutral) | 24 hours | 0 | 0 | 0 |
| 21 (male, | 1 hour | 0 | 0 | 0 |
| neutral) | 24 hours | 0 | 0 | 0 |
| 22 (female, | 1 hour | 0 | 0 | 0 |
| neutral) | 24 hours | 0 | 0 | 0 |
| 23 (female, | 1 hour | 0 | 0 | 0 |
| neutral) | 24 hours | 0 | 0 | 1 |
| 24 (female, | 1 hour | 0 | 0 | 0 |
| neutral) | 24 hours | 0 | 0 | 0 |
| 25 (female, | 1 hour | 0 | 0 | 0 |
| neutral) | 24 hours | 0 | 0 | 0 |
| 26 (female, | 1 hour | 0 | 0 | 0 |
| neutral) | 24 hours | 0 | 0 | 0 |
| 27 (female, | 1 hour | 0 | 0 | 0 |
| neutral) | 24 hours | 0 | 0 | 0 |
| 28 (female, | 1 hour | 0 | 0 | 0 |
| neutral) | 24 hours | 0 | 0 | 0 |
| 29 (female, | 1 hour | 0 | 0 | 0 |
| neutral) | 24 hours | 0 | 0 | 0 |
| 30 (female, | 1 hour | 0 | 0 | 0 |
| neutral) | 24 hours | 0 | 0 | 1 |

As a result, as shown in Table 11 above, the cream formulation containing the lyophilisate of the *Nelumbo nucifera* callus extract having an increased gallic acid content also had no skin irritation.

The invention claimed is:

1. A method for preparing a *Nelumbo nucifera* callus extract having an increased gallic acid content, the method comprising the steps of:
    (a) germinating a *Nelumbo nucifera* seed to obtain germinated *Nelumbo nucifera* tissue;
    (b) inducing a *Nelumbo nucifera* callus from the germinated *Nelumbo nucifera* tissue;
    (c) culturing the *Nelumbo nucifera* callus in a medium containing methyl jasmonic acid; and
    (d) extracting the *Nelumbo nucifera* callus culture having an increased gallic acid content.

2. The method of claim 1, wherein the medium contains the methyl jasmonic acid at a concentration of 100 to 400 µM.

3. The method of claim 1, wherein the gallic acid content of the extract obtained by the method is increased at least 10-fold compared to the gallic acid content of the extract of a *Nelumbo nucifera* callus cultured in a medium containing no methyl jasmonic acid.

4. The method of claim 1, wherein the *Nelumbo nucifera* is Ara Hongnyon lotus.

5. The method of claim 1, wherein the methyl jasmonic acid is added to the medium at 4 to 6 weeks from the start of the culturing in step (c).

* * * * *